United States Patent [19]

Pinori et al.

[11] Patent Number: 5,061,811
[45] Date of Patent: Oct. 29, 1991

[54] PROCESS FOR THE PREPARATION OF RETRO-INVERSO PEPTIDES AND 1,3-DIOXANE-4,6-DIONE INTERMEDIATES THEREOF

[75] Inventors: Massimo Pinori, Paderno D'Adda; Felice Centini, Rome; Antonio S. Verdini, Monterotondo, all of Italy

[73] Assignee: SCLAVO S.p.A., Siena, Italy

[21] Appl. No.: 450,572

[22] Filed: Dec. 14, 1989

[30] Foreign Application Priority Data

Dec. 23, 1988 [IT] Italy .............................. 23098 A/88

[51] Int. Cl.⁵ .......................................... C07D 319/04
[52] U.S. Cl. .................................... 549/274; 530/334
[58] Field of Search ......................................... 549/274

[56] References Cited

PUBLICATIONS

Huang et al., CA 108:75313m.
Brown et al., CA 86:105604d.

*Primary Examiner*—Jane T. Fan
*Attorney, Agent, or Firm*—Hedman, Gibson, Costigan & Hoare

[57] ABSTRACT

A method of synthesis of a partially retro-inverso peptide incorporating at least one malonyl residue of formula (III)

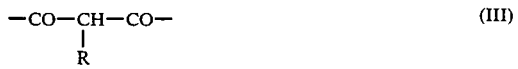

wherein R represents the side chain of an α-amino acid, is described which is characterized in that said malonyl residue is incorporated by condensing a 5-substituted-2,2-dimethyl-1,3-dioxane-4,6-dione of formula (VI)

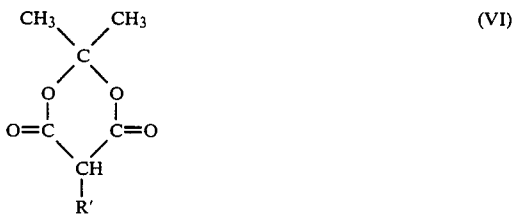

wherein R' is the side-chain R wherein the functional groups, if any, are suitably protected, with an amino acid, amino acid amide, peptide fragment, or pseudopeptide fragment wherein the terminal carboxyl group, if present, and the possible side-chain functionalities are suitably protected and the reactive amino group is trialkyl-silylated.

The new compounds of formula (VI) and a process for the preparation of a partially retro-inverso tuftsin analog which involves use of said method and said intermediate are also described and claimed.

3 Claims, No Drawings

PROCESS FOR THE PREPARATION OF RETRO-INVERSO PEPTIDES AND 1,3-DIOXANE-4,6-DIONE INTERMEDIATES THEREOF

The present invention relates to a new method of preparation of partial retro-inverso peptides and to the new intermediates used in such method.

"Retro-inverso" peptides are structural isomers of known peptides which differ therefrom in the direction of one or more amide linkages contained in the peptide sequence, which, in retro-inverso peptides, is reverted.

A "retro-inverso" peptide therefore will incorporate at least one grouping of formula (I)

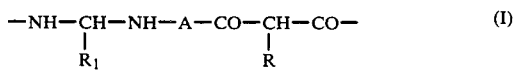

wherein R and $R_1$ represent the side chains of the suitable amino acids, and A represents nil or a peptide sequence containing at least one amino acid.

Reversal of said backbone peptide bond will be indicated, according to the internationally recognized terminology, as

wherein A has the same meaning as above, AAA and $AAA_1$ represent the standard three letter codes which identify the amino acids having a radical R and $R_1$, respectively, in the side chain, the prefix (g), immediately before the designation for the amino acid residue $AAA_1$, indicates that said amino acid residue has been replaced by the corresponding gem-diamino-alkyl derivative of formula (II)

while the prefix (m) indicates that the amino acid residue AAA has been replaced by the corresponding malonyl derivative of formula (III)

Reversal of one or more amide linkages generally stabilizes said bonds and the retro-inverso peptide which is thus obtained becomes more resistant toward enzymatic degradation.

If, in case of biologically active peptides, the interaction with biological receptors, which give rise to the particular activity, is essentially due to the side-chains, the retro-inverso analog will present the same pattern of biological activities of the so-called "parent peptide". Biological activity similar to the parent peptide coupled with a higher stability, will render the new compound of remarkable therapeutical interest.

For this reason, the retro-inversion approach has received a great deal of attention in the last few years and has been applied in a number of cases with a fair rate of success (see for instance the partial retro-inverso LH-RH analogs described in Int.J.Peptide Protein Res. 17, 1981, pp. 72–88; the partial retro-inverso enkephalinamides described in Science, 204, June 1979, pp.1210–12; the retro-inverso analogs of Substance P described in EP-A-161,007; the neurotensin analogs described in U.S. Pat. No.-A-4,716,149; $BPP_{5a}$ analogs described in EP-A-185433 and EP-A-190597; equine angiotensinogen 5-14 decapeptide fragment analogs described in EP-A-127,235 and EP-A-127,234; tuftsin analogs described in EP-A-253,190 and thymopentin analogs described in EP-A-282,891).

In general, the synthesis of retro-inverso peptides is carried out with methods which are substantially analogous to those conventionally employed for the preparation of peptides and which involve sequential condensation of the different residues (or fragments) present in the chain, differing therefrom for the introduction of at least one malonyl residue and at least one gem-diaminoalkyl residue.

Introduction of the gem-diaminoalkyl residue of formula (II) can be easily achieved by using, in the formation of the peptide bond with a free carboxyl group, the corresponding amide of formula (IV)

wherein $R_1'$ represents the side-chain $R_1$ wherein the functional groups, if any, are suitably protected, and then converting the terminal amido group in primary amino group by reaction with TIB (see Italian Patent Application no. 221281 A/81).

Introduction of a malonyl residue is actually carried out using 2-substituted malonic acid mono-esters of general formula (V)

wherein R'' is a lower alkyl group and R' represents the side chain R wherein the functional groups, if any, are suitably protected.

Said mono-esters (V) are obtained by monosaponification of the corresponding diesters which are prepared by conventional chemical processes for the preparation of 2-substituted malonates.

However, depending on the meaning of R', preparation of large amounts of mono-esters of high purity, as typically required in sequential processes, may be very difficult.

In general, in fact, preparation of the diester leads to a mixture of products from which the desired diester cannot be easily recovered unless chromatographic purification techniques are employed. Furthermore, owing to the poor stability of the mono-ester, its preparation by monosaponification of the diester, must be considered as part of the multistep process needed to incorporate it in the peptide sequence, process which involves, besides said monosaponification, activation, coupling and final saponification steps.

As an example, preparation of 2-(4-tert-butoxycarbonyl-amino-butyl)malonic acid mono ethyl ester, [(m)Lys(Boc)OEt], starting from 4-amino-1-butanol (a multi-step process which also includes chromatographic purification of the di-ester), occurs with overall yields lower than 20% (see P. V. Pallai et al., Biochemistry, 24, (1985), 1933–41).

Said procedure has the additional disadvantage of drastically limiting the choice of protecting groups in the overall strategy of synthesis, as these groups must be stable in the conditions used for the selective removal of the ester group from the incorporated malonyl residue.

Alternatively, the use of Meldrum's acid derivatives has been proposed a few years ago (see M. Goodman and M. Chorev in "Perspectives in Peptide Chemistry"- Ed. Eberle, Geyer & Wieland- (1981) - P. 283 et seq.), and, more particularly, the use of a 5-substituted-2,2-dimethyl-1,3-dioxane-4,6-dione of formula (VI)

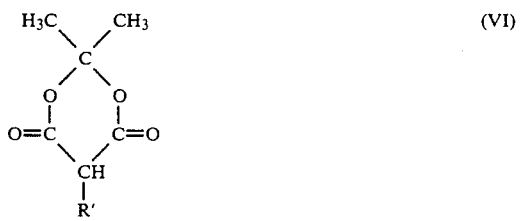

wherein R' represents the side-chain R wherein the functional groups, if any, are suitably protected.

In the actual practice, the efforts made to introduce a (m)Ala residue, using 2,2,5-trimethyl-1,3-dioxane-4,6-dione (the compound of formula (VI) wherein R' is methyl—Meldrum's acid 5-substituted with alanine side-chain—shortly indicated as (M)Ala), gave unsatisfactory results. In fact, only partial N-acylation of the amino acid partner has been observed and the desired pseudo-dipeptide has been obtained with low yields (see Italian patent application 23417 A/82). It has now surprisingly been found that Meldrum's acid derivatives of formula (VI) can satisfactorily be used in the preparation of retro-inverso peptides, to incorporate a malonyl residue (III), provided the condensation reaction "partner" is employed as the corresponding derivative tri-alkyl-silylated at the reactive amino nitrogen.

As a "partner" in the condensation reaction, an amino acid, an amino acid amide, a peptide fragment, or a pseudo-peptide fragment to which, in the desired pseudo-peptide sequence, the malonyl group must be linked and whose side-chain functionalities, if any, are suitably protected, can be employed.

It is apparent that, when a solid-phase condensation strategy is employed, said "partner" may be attached via the C-terminus to a suitably selected insoluble support as known in this field (Merrifield solid-phase peptide synthesis); in particular, in the solid-phase synthesis of retro-inverso peptides according to the most widely known method (see A. Pessi et al., J.Chem.Soc., Chem. Commun. (1983), 195), the compounds of formula (VI) are conveniently employed for the preparation of the necessary mono-malonyl amino acid amides.

For the purposes of the present invention, therefore, the term "N-tri-alkyl-silyl derivative" refers to the compound obtainable from an amino acid, an amino acid amide, a peptide fragment or a pseudo-peptide fragment, whose side-chain functional groups, if any, and whose terminal carboxy group, if any, are suitably protected, through activation of the amino group with a tri-alkyl-silyl group; said starting amino acid, amino acid amide, peptide fragment or pseudo peptide fragment optionally being anchored to an insoluble support.

The term "alkyl" identifies a straight or branched alkyl chain containing from 1 to 6 carbon atoms, and, preferably, methyl or ethyl.

Condensation of a compound of formula (VI) with the suitably selected N-trialkyl-silyl derivative, readily affords effective acylation of the amino group.

An additional advantage deriving from the use of this method to incorporate the malonyl residue, resides in the possibility, by simple hydrolysis of the obtained product at neutral or slightly acidic pH, of setting free the carboxyl group of the pseudo-peptide terminal malonyl residue, which is then available for the formation of the next amide bond.

In the actual practice, condensation between Meldrum's acid derivative (VI) and the suitably selected N-tri-alkyl-silyl derivative, is carried out by contacting a compound of formula (VI) wherein R' is as defined above, with at least an equimolar amount, and preferably a slight excess, of the N-tri-alkyl-silylated reaction partner.

The two reactants are contacted in the presence of an inert organic solvent. In general, polar, aprotic, organic solvents such as, for instance, halogenated aliphatic or aromatic hydrocarbons, e.g. methylene chloride, dichloroethane, chloroform, chlorobenzene, etc., cyclic or linear ethers, e.g. tetrahydrofuran, dioxane, diethyl ether, etc., and etherated glycols, e.g. ethylene glycol mono-methyl or mono-ethyl ether, can conveniently be employed.

Condensation is typically carried out at a temperature of from 0° C. to the reflux temperature of the reaction mixture and, preferably, at a temperature of from 15° to 50° C.

When condensation is complete, a mild acidic hydrolysis, using a diluted aqueous solution of an organic or inorganic acid, e.g. 5% or 10% citric acid, or 1% hydrochloric acid solution, affords the desired pseudo-peptide sequence incorporating a terminal malonyl residue with a free carboxyl group.

Any other step in the overall synthesis of the desired retro-inverso peptides, either before or after the introduction of the malonyl residue, may be carried out according to techniques widely known in peptide chemistry and conventionally employed in peptide synthesis.

The starting N-tri-alkyl-silylated derivative is conveniently prepared according to methods known in literature, using the conventional silylating agents.

Typically, said methods involve the use of tri-alkyl-silyl halides or N,O-bis-tri-alkyl-silylacetamides as the silylating agents.

In particular, as an example, the desired N-tri-alkyl-silyl derivatives can be prepared by reacting the suitably selected amino acid, amino acid amide, peptide or pseudo-peptide sequence, with at least an equimolar amount, but preferably an excess thereto, of N,O-bis-tri-alkyl-silylacetamide, in the presence of a polar and aprotic organic solvent which does not negatively interfere with the reaction course, at a temperature generally of from room temperature to the reflux temperature of the reaction mixture.

At the end of the silylation reaction, the obtained N-tri-alkyl-silylated derivative can be separated by conventional methods, e.g. by distillation or extraction.

Alternatively, and preferably, the condensation reaction is carried out directly adding the compound of formula (VI) to the mixture deriving from the silylation reaction.

In this case, to ensure that activation of the amino nitrogen proceeds quantitatively, silylation is preferably carried out using a strong excess of silylating agent, e.g. 2-3 moles of silylating agent per mole of substrate. Said excess is also useful to neutralize traces of humidity in the reaction mixture.

It is also possible, and this represents a further preferred embodiment of the present invention, to prepare the N-trialkyl-silyl derivative, directly in situ, when carrying out the condensation reaction. In this case the condensation reaction is carried out by contacting the compound of formula (VI) with the amino acid, amino acid amide, peptide or pseudo-peptide sequence with the free terminal amino group, and the silylating agent. Also in this case, preferably, a strong excess silylating agent is employed, while the reaction conditions are those reported above.

Some of the starting compounds of formula (VI), in particular those compounds of formula (VI) wherein R' represents the side chain of phenylalanine (R'=—CH$_2$—C$_6$H$_5$), alanine (R'=—CH$_3$), valine (R'=—CH(CH$_3$)$_2$), isoleucine (R'=—CH(CH$_3$)CH$_2$CH$_3$), glutamic acid γ-ethyl ester (R'=—CH$_2$CH$_2$COOC$_2$H$_5$) and tryptophan (R'=—CH$_2$(3-indolyl)), are known compounds which can be synthesized according to methods known in literature.

In general, however, all the compounds of formula (VI) can be prepared by alkylation of the 5-positioned carbon atom of Meldrum's acid of formula (VII)

(VII)

with methods which differ depending on the structure of the substituent R' which has to be introduced.

As an example, one of such methods is the reaction of Meldrum's acid (VII) with ketones or aromatic or α-branched aliphatic aldehydes, to afford Knoevenagel-like products which are then easily reduced with sodium borohydride to yield 5-alkyl substituted Meldrum's acids (A. D. Wright et al., Tetrahedron Lett., pp.1759-62).

Using linear aliphatic aldehydes, Knoevenagel-like products cannot be isolated because the process mainly affords bis-adducts deriving from a subsequent Michael reaction; in this case therefore a one-pot reductive alkylation of Meldrum's acid is carried out using a reducing agent which selectively acts on double bonds (D. M. Hrubowchak et al., Tetrahedron Lett., (1979), pp. 2325-6).

An alternative method for synthetizing these compounds consists in the Michael addition of the Meldrum's acid anion to electrophilic olefins (Cheng-Chu Chan et al., Synthesis, (1984), pp. 224-5).

The procedures actually employed for the preparation of the compounds of formula (VI) are substantially those described in the above cited references with optional minor modifications, apparent to any chemist, which are made to fit the methods to the particular substrates.

As for the protecting groups which may be present on the 5-positioned substituent, the protecting groups of the side-chain functionalities known in literature and conventionally employed in peptide syntheses can be used. In some cases, there might be some limitations to the protecting groups of the radicals which must be introduced at the 5-position, due to the particular process employed for the preparation of the compound of formula (VI).

It is however always possible, once the 5-substituted Meldrum's acid derivative has been synthetized, to replace the protecting group employed in the preparation of this product with a different one, mostly suitable for peptide synthesis.

The process of the present invention may be employed for the synthesis of any peptide containing at least one retro-inverso peptide bond. In particular, optimum results have been obtained in the synthesis of the tuftsin analog, described in EP-A-253,190, which contains a retro-inversion at the Thr-Lys bond.

It represents therefore a further object of the present invention a process for the synthesis of a peptide of formula

characterized in that incorporation of the malonyl residue of formula

is carried out using a 5-substituted Meldrum's acid of formula (VIa)

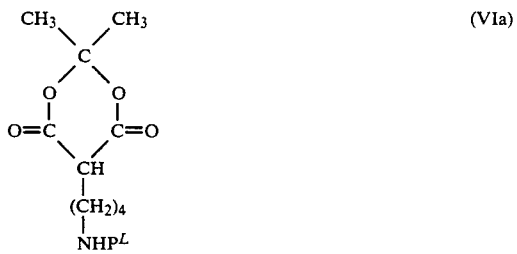

wherein P$^L$ is a protecting group of lysine amino function.

As anticipated P$^L$ is any of the conventional amino protecting groups and, preferably, trifluoroacetyl, tert-butoxycarbonyl, tert-amyloxycarbonyl, or optionally nitro- or halo-substituted benzyloxycarbonyl.

The compounds of formula (VIa) are conveniently prepared starting from 4-amino-butyraldehyde diethyl acetal. In particular, the compound of formula (VIa) wherein P$^L$ is a trifluoroacetyl group has been prepared through N-acylation of 4-amino-butyraldehyde diethyl acetal with trifluoroacetic anhydride, followed by hot hydrolysis of the obtained 4-trifluoroacetamido-butyraldehyde diethyl acetal in slightly acidic aqueous solution. A mixture of products is obtained which may be employed as such in the reductive alkylation of Meldrum's acid (VII) affording the compound of formula (VIa) wherein P$^L$ is a trifluoroacetyl group.

If desired, alkaline hydrolysis of the trifluoroacetyl group followed by reaction with a different acylating agent can easily afford any other compound (VIa).

According to a particularly preferred embodiment, the process for preparing the tuftsin analog retro-inverted at the Thr-Lys bond involves:

a) condensing the compound of formula (VIa) with the Nα-tri-alkyl-silyl derivative of (D)-threonineamide wherein the hydroxy group is suitably protected by a protecting group $P^T$, b) hydrolysing in mild acidic conditions the thus obtained product to afford a fragment of formula (VIII)

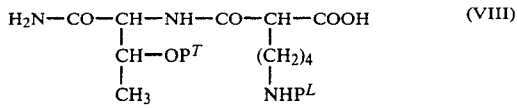

wherein $P^T$ and $P^L$ are as defined above, c) condensing the fragment of formula (VIII) with a dipeptide fragment of formula (IX)

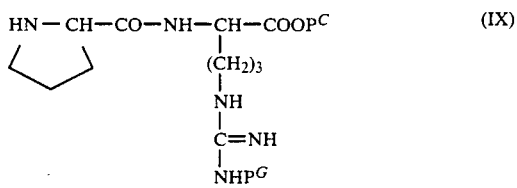

wherein $P^C$ is a carboxyl protecting group and $P^G$ is an arginine guanidino protecting group, d) converting the terminal threonine amide group into an amino group by treatment with TIB and e) removing all the protecting groups.

Other retro-inverso peptides which are conveniently prepared by the method of the present invention, wherein the malonyl residue is incorporated by condensing the corresponding 5-substituted Meldrum's acid derivative with the suitably selected N-tri-alkyl-silyl derivative, are desmorphin retro-inverso analog described in Chemical Abstracts 103 178616, and thymopentin (TP5) retro-inverso analog described in EP-A-282,891. While in the latter case a Meldrum's acid derivative of formula (VIa) has been employed, in the former case the starting Meldrum's acid derivative has the following formula (VIb)

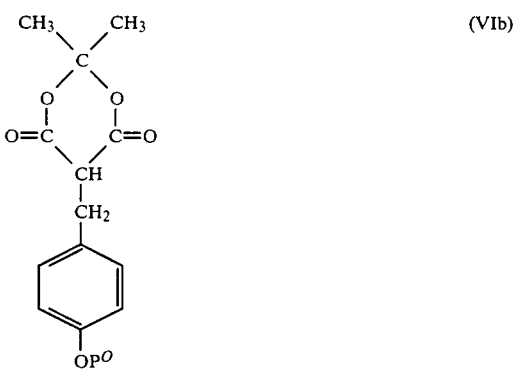

wherein $P^O$ is a protecting group of tyrosine hydroxy function. Also in this case any protecting group, conventionally employed in peptide synthesis for the protection of tyrosine hydroxy group, can suitably be employed. Particularly preferred groups are however tert-butyl, tert-amyl, benzyl, optionally halo- or nitro-substituted, and triflucroacetyl.

A further object of the present invention are therefore the new compounds of formula (VI), and in particular the new compounds of formula (VIa) and (VIb), useful as intermediates in the synthesis of retro-inverso peptides.

The following examples which are only aimed at better illustrating some representative embodiments of the present invention should not be interpreted as a limitation to the scopes thereof.

EXAMPLE 1

$[(g)Thr^1,(R,S)(m)Lys^2]$tuftsin acetate 1) (M)Lys(TFA)

(2,2-dimethyl-1,3-dioxane-5-(4-trifluoroacetamido-butyl)-4,6-dione)

Dimethylaminopyridine (25.6 g, 210 mmol) and, dropwise, a solution of trifluoroacetic anhydride (29.4 ml, 210 mmol) in methylene chloride (100 ml) are added to a solution of 4-aminobutyraldehyde diethyl acetal (32.2 g, 200 mmol) in methylene chloride (600 ml) cooled to 0° C. and kept under stirring. The mixture is stirred at 0° C. for additional 30 minutes, the precipitate which forms is removed by filtration and the filtrate is washed with water (4×200 ml). The organic phase is dried over $Na_2SO_4$ and evaporated under vacuum affording an oily product (48 g). 1N HCl (500 ml) is then added thereto under vigorous stirring, and stirring at room temperature is continued until a homogeneous solution forms (about 15 minutes). The solution is then cooled and the pH is brought to 6 by the addition of 1N NaOH. The solution is then heated to 100° C. for 15 minutes, cooled and brought to a small volume (about 200 ml) under vacuum. The solution is extracted several times with methylene chloride and the organic extracts, pooled, are dried over $Na_2SO_4$ and evaporated under vacuum yielding an oily residue (27 g) containing 60% by weight of 4-trifluoroacetamido-butyr-aldehyde.

The obtained product is added to a solution of sodium cyanoborohydride (3.3 g, 52 mmol) and 2,2-dimethyl-1,3-dioxane-4,6-dione (Meldrum's acid) (12 g, 84 mmol) in N,N'-dimethylformamide (DMF) (50 ml).

After stirring at room temperature for 1 h, water (150 ml) is added thereto and pH is brought to 4.5 affording a precipitate which is recovered by filtration, washed with a small amount of cold water and then with ethyl ether and finally dried under vacuum. The yield is 17.5 g (28%), m.p. 131°–2° C.

Elemental analysis % Calculated for $C_{12}H_{16}O_5NF_3$:C 46.3; H 5.15; N 4.5; % Found C 46.5; H 5.3; N 4.6;

Mass and $^1$H-NMR analyses confirm the assigned structure.

2) HO(m)Lys(TFA)-D-Thr(Bu$^t$)NH$_2$ (N,2-(4-trifluoroacetamido)butyl-malonyl-(O)-tert-butyl-(D)-threoninecarboxamide N,O-bis-trimethylsilylacetamide (8.1 g, 40 mmol) is added to a solution of O-tert-butyl-D-threoninecarboxamide (3.5 g, 20 mmol) in methylene chloride (90 ml) and the solution is refluxed under stirring for 6 h. After cooling the solution to room temperature, the product obtained in step 1) above (5.6 g, 18 mmol) is added thereto and the reaction mixture is stirred for 18 h. The mixture is washed a few times with 5% citric acid aqueous solution, the solvent is evaporated off and the thus obtained residue is triturated with a water/acetone mixture. An amorphous solid (5.2 g) is obtained whose identity has been confirmed by $^1$H-NMR and mass (electronic impact) analyses.

3) [(m)Lys-D-Thr(Bu$^t$)NH$_2$]-Pro-Arg-OH

The product obtained in the foregoing step (2.1 g. 5 mmol) is dissolved in methylene chloride (30 ml)/DMF (4 ml), the obtained solution is cooled to 0° C. and N-hydroxybenzotriazole (HOBt) (0.67 g, 5 mmol) and N,N'-dicyclohexylcarbodiimide (DCC) (1 g, 5 mmol) are then stirred in. After stirring at 0° C. for 30 minutes and at room temperature for additional 30 minutes, N,N'-dicyclohexylurea (DCU) that forms is removed by filtration and HCl·Pro-Arg(NO$_2$)-OBz (2.2 g, 5 mmol) (prepared as described by M. Fridkin et al. in Biochim. Biophys. Acta, 496, pp.203–11, (1977)) and triethylamine (0.7 ml, 5 mmol) are added to the filtrate.

After stirring at room temperature for 18 h, the filtrate solution is evaporated under vacuum, the residue is taken up in AcOEt (100 ml) and the thus obtained solution is washed in succession with 5% NaHCO$_3$ solution, 10% citric acid solution and water.

The organic phase is dried over Na$_2$SO$_4$ and the solvent is evaporated off yielding a solid (3.8 g) which is then dissolved in methanol (50 ml). Palladium sponge (4 g) and ammonium formate (0.95 g, 15 mmol) are added to the thus obtained solution. The mixture is stirred gently for 2 h at room temperature, the catalyst is then removed by decantation and washed with methanol.

The methanol phases are combined and evaporated under vacuum to a volume of about 20 ml. Water (30 ml) is then added thereto and pH is brought to 12 by the addition of 1N NaOH. After 45 minutes at room temperature, the pH of the solution is adjusted at 5 by the addition of 1N HCl, the solution is partially evaporated under vacuum and lyophilized from water few times.

The desired product is then obtained by reverse-phase displacement chromatography of the solid residue, using a Lichroprep ® RP-18 column as the stationary phase, 0.1% trifluoroacetic acid aqueous solution as the carrier and 50 mM benzyl-tributyl-ammonium chloride as the displacer. Titer and purity of the components of the mixture in the different fractions are evaluated by reverse-phase HPLC. Working on an aliquot of the raw solid (1.2 g), the pure compound (0.92 g) is obtained whose identity has been confirmed by $^1$H-NMR and mass (FAB) analyses.

4) (AcOH)$_2$·H-(g)Thr-(m)Lys-Pro-Arg-OH ({(2)-2[N-(1-amino-2-hydroxy-propyl)carbamyl]-6-amino}hexanoyl-L-prolyl-arginine diacetate)

The compound obtained in the preceding step (0.7 g, 1 mmol) is dissolved in acetonitrile/water 1/1 (40 ml) and I,I-bis-trifluoroacetoxy-iodo-benzene (TIB) (0.56 g, 1.3 mmol) is stirred in under nitrogen atmosphere. After stirring for 6 h, the mixture is evaporated under vacuum and the obtained residue is suspended in concentrated HCl and kept at 0° C. for 8 minutes. The mixture is then evaporated under vacuum a few times, taking up the residue in water, and finally it is lyophilized. The thus obtained residue is then purified by chromatography on a CM-Sephadex C-25 (2.6×30 cm) column, eluting with a linear gradient of 0.05–0.5M ammonium acetate, flow rate 5 ml·min$^{-1}$ to a total volume of 2 l.

Lyophilization of the pure fractions affords a solid (0.31 g) whose structure has been confirmed by $^1$H-NMR and mass (FAB) analyses.

EXAMPLE 2

[(g)Arg$^1$, (R,S)(m)Lys$^2$]TP5 acetate

1) (M)Lys(Boc)

(2,2-dimethyl-5-(4-tert-butoxycarbonylamino-butyl)-1,3-dioxane-4,6-dione)

A solution of the compound obtained in step 1) of Example 1 -/(M)Lys(TFA)] (6.22 g, 20 mmol) in water (50 ml) is brought to pH 12.5 by the addition of 2N NaOH. The mixture is stirred at room temperature for 30 minutes and then cooled to 0° C. A solution of di-tert-butyl-carbonate (8.72 g, 40 mmol) in dioxane (75 ml) is added thereto and the reaction mixture is allowed to warm up to room temperature and stirred for 2 h keeping the pH at 9. Dioxane is evaporated off under reduced pressure and the aqueous solution is washed with n-hexane. The pH is brought to 3.5 by the addition of citric acid and the solution is extracted few times with methylene chloride. The organic extracts are pooled, dried over Na and evaporated to afford a white solid (5.4 g, 86%) with m.p. 112°–3° C.

$^1$H-NMR confirms the assigned structure.

2) Ho(m)Lys(Boc)-Asp(Bu$^t$)-Val-Tyr(Bu$^t$)OBu$^t$

A solution of ammonium formate (1.3 g, 20 mmol) in methanol (20 ml) and palladium sponge (3.5 g) are added under nitrogen atmosphere to a solution of Z-Asp(Bu$^t$)-Val-Tyr(OBu$^t$)-OBu$^t$ (prepared as described in Example 1 step 3) of EP-A-282,891) (4.94 g, 7 mmol) in methanol (80 ml). The resulting solution is heated for a short period of time to 40° C. and then kept at room temperature for 1 h. The mixture is allowed to settle, then it is filtered on celite, washing the solid on filter with methanol. The solvent is evaporated off, and the obtained residue is taken up in AcOEt. The organic solution is washed with 10% Na$_2$CO$_3$ solution, with water, and finally dried on MgSO$_4$.

Evaporation of the solvent gives the compound H-Asp(Bu$^t$)-Val-Tyr-(Bu$^t$)OBu$^t$ as an oily product (3.75 g, 6.66 mmol).

Tri-methyl-chloro-silane (0.825 ml, 6.66 mmol) is added to a solution of the thus obtained product, the compound prepared according to step 1) above (2.3 g, 7.32 mmol), and N,O-bis-trimethylsilyl-acetamide (3.33 ml, 13.32 mmol) in tetrahydrofuran (60 ml). The reaction mixture is allowed to stand at room temperature overnight, then the solvent is removed and the residue is taken up in methylene chloride. The solution is washed with aqueous citric acid pH 4, dried over MgSO$_4$ and brought to a small volume. Addition of AcOEt/n-hexane precipitates the desired product (4.35 g, 76%).

$^1$H-NMR and FAB-MS analyses confirm the assigned structure.

3) [(m)Lys(Boc)-(D)-Arg(Mtr)NH$_2$]-Asp(Bu$^t$)-Val-Tyr(-Bu$^t$)-OBu$^t$

The compound obtained in the foregoing step (1.23 g, 1.5 mmol) and HOBt (0.202 g, 1.5 mmol) are dissolved in methylene chloride (30 ml) containing DMF (1 ml) cooled to 0° C., and DCC (0.309 g, 1.5 mmol) is added to the obtained solution. After 30 minutes at 0° C., the reaction mixture is brought to room temperature and stirred for additional 30 minutes. DCU is then filtered off and N$^G$-(4-methoxy-2,3,6-trimethyl)benzenesolfonyl-D-arginine-amide (0.580 g, 1.5 mmol) is added to the remaining solution. The reaction mixture is allowed to stand at room temperature overnight, then the solvent is removed, the residue is taken up in AcOEt, the organic solution is washed in succession with 5% NaHCO$_3$ solution, 10% citric acid solution, and water. The solution is dried over MgSO$_4$, the solvent is evaporated off and the residue is triturated with n-hexane, yielding the desired product (1.63 g, 90%).

4) AcOH H-(g)Arg-(R,S)[m]Lys-Asp-Val-Tyr-OH

The compound of the foregoing step (1.187 g, 1 mmol) is dissolved in H$_2$O/CH$_3$CN/DMF (35/60/5) (20 ml) and, while keeping the solution under nitrogen atmosphere, TIB (0.473 g, 1.1 mmol) is added thereto. The mixture is kept at room temperature overnight, then evaporated; the residue is taken up in ethyl ether and the solution is evaporated again. This last procedure is repeated three times, then a mixture of trifluoroacetic acid/trifluoromethanesulfonic acid/ethanedithiol (89/1/10) (60 ml) cooled to 0° C. is added thereto. After 10 minutes at 0° C., triethylamine (0.9 ml) is added, the temperature is brought to 40° C. and the mixture is evaporated under a nitrogen stream. The residue is taken up in water (100 ml) and washed with ethyl ether (100 ml). The organic phase, in its turn, is washed with water (50 ml) and the aqueous phases are combined, washed again with ethyl ether (3 x 50 ml) and lyophilized. Purification of the thus obtained product by ion exchange chromatography is carried out as described in Example 1, step 11 of EP-A-282,891.

EXAMPLE 3

Retro-inverso analog of desmorphin

H-Tyr-D-Ala-(g)Phe-Gly-(m)Tyr-Pro-Ser-NH$_2$ 1) (M)Tyr(Bu$^t$)

(2,2-dimethyl-5-(4-tert-butoxy)benzyl-1,3-dioxane-4,6-dione)

N,N-dimethylformamide di-tert-butyl acetal (48 ml, 200 mmol) is added (0.1 ml/min) to a solution of 4-hydroxybenzaldehyde (6.1 g, 50 mmol) in benzene (50 ml) kept under nitrogen atmosphere at 80° C. The mixture is then cooled to room temperature and evaporated under reduced pressure. The residue is dissolved in methylene chloride, washed with 5% NaHCO$_3$ solution and then with water, dried over Na$_2$SO$_4$ and evaporated to a dark oil. Said oil is purified on a silica gel column eluting with AcOEt/n-hexane 2/8 (v/v). The purified product (5 g, 28 mmol) is added to a solution of Meldrum's acid (4.46 g, 31 mmol) and piperidine (0.6 ml, 6 mmol) in DMF (30 ml). After stirring at room temperature for 3 h, the solvent is evaporated off under reduced pressure and the residue is dissolved in methanol (50 ml). Solid NaBH$_4$ (1.14 g, 30 mmol) is gradually added to the thus obtained solution within 15 minutes, then the reaction is stopped by the addition of water (100 ml) and 1N HCl up to pH 3. The resulting precipitate is recovered by filtration, washed with cold water, dried under vacuum and triturated with hexane yielding 6.12 g (40%) of (M)Tyr(Bu$^t$) (Meldrum's acid derivative of formula (VIb) wherein P$^O$ is a tert-butyl group) with m.p. 75°–7° C.

The $^1$H-NMR analysis confirms the assigned structure.

The compound of the foregoing step is employed in the synthesis of the compound of the title by following substantially the scheme reported in Chemical Abstracts 103 178616p, with the difference that the (m)Tyr residue is incorporated by condensing the N-trimethylsilyl derivative of the fragment H-Gly[Z-D-Ala-(g)Phe] with the compound obtained in step 1) above.

The condensation reaction is carried out substantially as described in step 2) of Example 2.

We claim:

1. A 5-substituted-2,2-dimethyl-1,3-dioxane-4,6-dione of formula (VI)

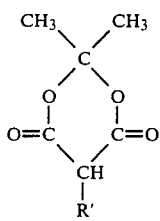

wherein R' represents —CH$_2$—CH$_2$—CH$_2$—CH$_2$—NH$_2$, the side-chain of the amino acid lysine, or

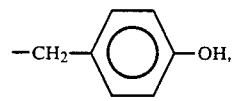

the side-chain of the amino acid tyrosine, wherein the functional groups are suitably protected.

2. A compound of claim 1 wherein R' is —CH$_2$—CH$_2$—CH$_2$—CH$_2$—NH$_2$, the side-chain of the amino acid lysine, wherein the amino group is protected with a group selected from trifluoroacetyl, tert-butoxy-carbonyl, tert-amyloxycarbonyl, and, optionally nitro- or halo-substituted, benzyloxy-carbonyl.

3. A compound of claim 1 wherein R' represents

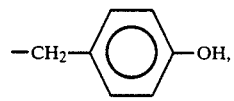

the side-chain of the amino acid tyrosine, wherein the hydroxy group is protected with a group selected from tert-butyl, tert-amyl, benzyl, halo- or nitro-substituted benzyl, and trifluoroacetyl.

* * * * *